United States Patent [19]
Pietronigro

[11] Patent Number: 5,162,115

[45] Date of Patent: * Nov. 10, 1992

[54] ANTINEOPLASTIC SOLUTION AND METHOD FOR TREATING NEOPLASMS

[76] Inventor: Dennis D. Pietronigro, R.F.D. 2 Box 319, Lakeside Dr., Yorktown Heights, N.Y. 10598

[ * ] Notice: The portion of the term of this patent subsequent to Sep. 24, 2008 has been disclaimed.

[21] Appl. No.: 763,122

[22] Filed: Sep. 20, 1991

Related U.S. Application Data

[63] Continuation of Ser. No. 349,410, May 9, 1989, Pat. No. 5,051,257.

[51] Int. Cl.$^5$ ............ A61K 9/08; A61K 43/00; A61K 45/06; A01N 25/02
[52] U.S. Cl. ............ 424/423; 424/1.1; 424/422; 424/424; 424/425; 424/426; 424/427; 424/428; 424/405; 514/937
[58] Field of Search ............ 424/1.1, 422, 423, 424, 424/425, 426, 427, 428, 405; 514/937

[56] References Cited

U.S. PATENT DOCUMENTS

5,051,257  9/1991  Pietronigro .............. 424/423

Primary Examiner—Thurman K. Page
Assistant Examiner—Carlos Azpuru
Attorney, Agent, or Firm—Barry R. Blaker

[57] ABSTRACT

Disclosed are antineoplastic for direct intratumoral delivery. The solutions are formulated using antineoplastic solutions agents dissolved in organic, water miscible, solvent vehicles. The vehicle is selected such that a) the agent is dissolved in the vehicle, b) the agent is stable and bioavailable in the vehicle, and c) the vehicle readily diffuses through and permeates tumorous tissue. The solution is injected directly into the tumor and, as the vehicle permeates the tumor tissue it transports the agent therewith. In this way therapeutically effective levels of antineoplastic agent are effectively and rapidly delivered and disseminated into the tumor mass with little or no dissemination into surrounding healthy tissue.

35 Claims, 1 Drawing Sheet

ANTINEOPLASTIC SOLUTION AND METHOD FOR TREATING NEOPLASMS

CROSS REFERENCE

This application is a continuation of copending application Ser. No. 07/349,410 filed May 9, 1989, now U.S. Pat. No. 5,051,257 granted on Sept. 24, 1991.

FIELD OF THE INVENTION

This invention relates to a method for formulating antineoplastic solutions for the treatment of neoplasms. In another aspect it relates to a novel method for the treatment of neoplastic disease.

BACKGROUND

The effective treatment of cancer remains a top priority for the medical establishment. Great strides have been made in the effective therapy of some systemically disseminated forms involving the blood tissues, for instance, childhood leukemia and Hodgkin's disease. However, progress in treating the most prevalent forms of solid malignant masses, of, for instance, the lung, colon, rectum and breast, as well as other less prevalent but aggressive forms, such as primary brain tumors, melanomas and the like, has been slow. This is so despite a major effort by the medical community wherein multitudinous therapeutic protocols using surgical excision, radiation therapy, chemotherapy and immunotherapy, either as individual modalities or in various combinations, have been tested in experimental models and/or clinically.

One major problem with drug therapy which has heretofore remained unresolved is one of selectivity, in other words, attainment of effective treatment of the tumor without causing damage to healthy surrounding tissues or organs. There are two general methods heretofore known by which to achieve this end: a) using an agent which is selectively toxic to the tumor, or b) selectively delivering a toxic agent to the tumor. Unlike penicillin or other antibiotics that selectively kill bacteria without damaging normal human tissues, the search for a cancer treatment "magic bullet" has remained elusive. Immunotherapy approaches using monoclonal antibodies, cytotoxic immune cells and/or other biologic response modifiers hold promise in this regard, but have thus far also demonstrated host toxicities as well as a variety of other problems The usefulness of chemotherapeutic agents delivered systemically is severely limited due to the small amount of drug reaching the tumor and such host toxicities as myelosuppression or gastrointestinal toxicity and a variety of organ specific toxicities, such as, cardiotoxicity with adriamycin, kidney toxicity with cis-platinum and lung toxicity with bleomycin. These complications restrict both the total dosage and the number of treatments patients can tolerate. Moreover, certain therapeutic agents exhibit relatively short effective lives in the presence of body fluids and often reach the tumor in a partially or entirely deactivated condition when introduced systemically.

Regional delivery has been tested as a method of increasing the ratio of therapeutic agent delivered to the tumor versus that delivered to systemic sites of toxicity. Methods have included intra-arterial injection into arteries serving the area of the tumor, as exemplified by such techniques as liver perfusion, intraperitoneal delivery by injection or implanted delivery devices for tumors in the peritoneal cavity, delivery into cerebrospinal fluid by injection or implantable device for central nervous system tumors, intra-cavitary delivery by injection or implantable device following surgical resection and delivery by devices implanted near the tumor. These methods have also met with only limited success.

Direct intratumoral delivery offers promise, as an optimal method for delivering large quantities of antineoplastic agents to solid tumor masses while minimizing delivery to the systemic sites of toxicity. Direct intratumoral delivery has been tested on many tumor types. A wide variety of antineoplastic agents including chemotherapeutics, biotherapeutics and radiotherapeutics have been used. For example, Livraghi and co-workers, *Tumori* 72 (1986), pp. 81–87 have studied the effect of direct intratumoral chemotherapy in humans under ultrasound guidance. They administered standard aqueous formulations of 5-fluorouracil, methotrexate and cyclophosphamide. Tator and co-workers, *Cancer Research* 27 (1977), pp. 476–481 studied the effect of stereotactic intratumoral injection of two nitrosoureas, i.e., 1-(2-chloroethyl)-3-cyclohexyl-1-nitrosourea (CCNU), and 1-(2-chloroethyl)-3-(trans-4-methylcyclohexyl)-1-nitrosourea (Me-CCNU) in a mouse ependymoblastoma model. These investigators tested various vehicles which might allow them to treat the tumor with very large drug doses. In their most suitable formulation these water insoluble nitrosoureas were suspended in 0.4% aqueous methylcellulose. Their experiments, sometimes using a series of up to ten separate, temporally spaced, injections into a single tumor mass produced only modest increases in life span.

The most significant problem limiting these and other direct intratumoral therapy methods resides in the inability to deliver lethal levels of antineoplastic substance throughout the entire tumor mass. Stability and bioavailability of cytotoxic substances in the delivery vehicles has also been a problem.

In view of the above, the limitations to the treatment of cancer known to the prior art are readily apparent

OBJECTS OF THE INVENTION

Accordingly it is an object of the present invention to provide a novel method for the treatment of neoplastic disease.

It is another object of the present invention to provide an efficacious method for the direct intratumoral delivery of antineoplastic solutions.

Yet another object of the present invention is to provide efficacious antineoplastic solutions for direct intratumoral delivery.

Other objects and advantages of the present invention will, in part, be obvious and will, in part, appear hereinafter.

The manner in which these and other objects are realized by the present invention will be apparent from the summary and detailed description set forth below.

SUMMARY OF THE INVENTION

In accordance with the present invention, antineoplastic solutions for direct intratumoral injection are formulated consisting essentially of an antineoplastic agent solute as the primary active ingredient and a water miscible organic solvent vehicle The solvent vehicle is selected such that, a) in addition to being soluble in water it also readily diffuses through biological membranes, thereby causing it to readily permeate tumor masses, b) the antineoplastic agent is soluble to therapeutically effective levels therein and c) the antineoplastic agent is stable and bioavailable therein. By direct intratumoral injection of such antineoplastic solutions the vehicle transports therapeutically effective concentrations of the dissolved active antineoplastic agent throughout at least a substantial volume of the tumor mass and with minimal invasion of surrounding healthy tissues. The advantages of the present invention will become clear after consideration of the following detailed description of the invention, including the tables and drawing hereof.

DETAILED DESCRIPTION OF THE INVENTION

As indicated above, according to the present invention, antineoplastic solutions for direct intratumoral delivery are formulated consisting essentially of antineoplastic agent solutes and organic, water miscible, solvent vehicles. The vehicle serves to transport therapeutically effective levels of the antineoplastic agent throughout at least a substantial volume of the mass of the tumor. This is accomplished by selecting the water miscible organic solvent vehicle such that a) the vehicle readily diffuses through cell membranes, thereby to permeate the tumor, b) the agent is soluble in the vehicle to therapeutically effective levels, and c) the agent is stable and bioavailable in the vehicle.

According to the present invention the solvent vehicles for direct delivery and cellular transport of antineoplastic agents are water miscible organic solvents which are soluble in water and which also partition and diffuse into and through biological cell membranes from aqueous solutions. Their usefulness is based not only upon their solvent power for the therapeutic agent, but also upon their ability to permeate the tumor effectively. In the solvent vehicles of the invention molecular movement through the aqueous phase is driven by their high water solubility which, in a preferred embodiment, is infinite or nearly so at physiologic conditions. Since the majority of tumor substance is aqueous, water miscibility or solubility of the organic solvent component is important. Additionally, the water miscible organic vehicles of the present invention have sufficient lipophilicity to move into cellular membranes from aqueous solution Molecular characteristics that endow this ability are molecular weight of less than about one thousand Daltons, measured as described in Morrison and Boyd, Organic Chemistry, pp. 412-413, Allyn and Bacon Inc., Boston, 1966, and electrical neutrality (that is, absence of charge) as demonstrated by molecular formula. A direct measure of molecular movement from aqueous solution into lipids is the partition coefficient as described, for example, by Cornford et al., "Comparison of lipid-mediated blood-brain-barrier penetrability in neonates and adults", in *American Journal of Physiology* 243 (1982), pp. C161-C168. The preferred water miscible organic solvents of the present invention have partition coefficients of at least about 0.1. Cornford et al., supra, also demonstrate the close correlation between partition coefficients and true cellular membrane diffusivity measurement using the brain uptake index. Exemplary water miscible organic solvents possessing the foregoing characteristics and which are therefore useful as direct delivery vehicles in the present invention are: methanol, ethanol, 1-propanol, 2-propanol, 1-propen-3-ol (allyl alcohol), 2-methyl-2-propanol (tertiary butyl alcohol), diacetone alcohol, N,N,-dimethylformamide, dimethylsulfoxide, 1,3-dioxane, acetone, pyridine, tetrahydrofuran, ethylene glycol and propylene glycol. I have found ethanol to be particularly useful. In addition to these, other useful organic solvent vehicles can also be identified by their water solubility and biological membrane diffusivity. In contrast to the alcohols specifically listed above, the usefulness of 1-butanol would be somewhat limited while the use of aliphatic alcohols higher than C4 would be contraindicated for use in the invention due to the limited water solubilities thereof.

Aqueous vehicles are ineffective as direct delivery solvent vehicles in the antineoplastic solutions of the present invention because water does not adequately diffuse into and through cellular membranes and, therefore, cannot effectively transport the antineoplastic agent component through the tumor mass. Because water has poor diffusivity through cell membranes, as indicated above, the effectiveness of transport of an antineoplastic agent dissolved in an aqueous vehicle will depend solely upon the cellular membrane diffusivity characteristics of the agent itself, that is to say, upon its own ability to dissolve in water and diffuse through cell membranes. Additionally, if it is desired to treat a tumor mass with very high agent levels from aqueous formulations, logic dictates that antineoplastic agents of high water solubility must be employed. Such agents, by their very nature, tend to have poor cell membrane diffusivity and, therefore, do not themselves significantly permeate the tumor mass. If, on the other hand, one uses an aqueous solution of an antineoplastic agent which itself permeates tissue nicely, for instance, as in the case of 1,3-bis(2-chloroethyl)-1-nitrosourea (BCNU), one must use solutions having relatively low agent concentrations due to the inherently low water solubility of such agents. In addition, many known antineoplastic agents, such as BCNU, are not very stable in aqueous solution but are far more stable in the organic water miscible solvent vehicles of the present invention.

Lipoidal substances such as animal oils are also not effective as the organic solvent component in the present invention. Such lipoidal solvents are not generally adequately miscible in water and, therefore, are generally deficient in their molecular movement through the aqueous phase of the tumor mass. Moreover, antineoplastic agents with high solubilities in lipoidal substances will usually have poor tumor diffusion characteristics due to their generally inherently low water solubility.

Where the antineoplastic agent to be employed can remain effectively stable, bioavailable and can be solubilized to therapeutically effective concentrations, and where the organic water miscible solvent vehicle can maintain its tumor permeating ability in the presence of aqueous or lipoidal substances, said solvent vehicle can also tolerate the presence therein of such aqueous or lipodal substances. Accordingly, where this circumstance is encountered, I specifically contemplate that the water miscible organic solvent vehicles of the present invention can also contain such aqueous or lipoidal substances up to that concentration at which significant loss of: a) the solvent's ability to permeate the tumor, or b) stability, bioavailability or solubility of the antineoplastic agent occurs. Obviously, the maximum concentration of aqueous or lipoidal substances to be tolerated in the organic water miscible solvent vehicles of the invention can vary widely as a function of the specific aqueous and/or lipoidal substance(s) to be included, the specific antineoplastic agent, the organic solvent vehicle, and the antineoplastic agent concentration to be formulated. Thus, it is not possible to state a specific maximum tolerable concentration of such aqueous or lipoidal substances in the organic solvent vehicles which will be valid for all possible antineoplastic solutions within the scope of the invention.

The antineoplastic agents that can be formulated into effective direct delivery antineoplastic solutions according to the present invention include chemotherapeutics, biotherapeutics and radiotherapeutics exhibiting cytotoxic or cytostatic activity. By using the methods disclosed, therapeutically effective doses of substantially any antineoplastic agent solute can be delivered throughout an at least substantial volume of the mass of a tumor without regard to the exact nature of the antineoplastic agent or its molecular mechanism of action (excluding the case, of course, wherein extratumoral activation of the agent is necessary). Useful chemotherapeutic agents include alkylating agents, such as platinum coordination compounds, nitrogen mustards, nitrosoureas, ethyleneimine derivatives, alkyl sulfonates and triazenes, antimetabolites, such as folic acid analogs, pyrimidine analogs, and purine analogs; vinca alkaloids; antibiotics; hormones, such as adrenocorticosteroids, progestins, estrogens and androgens; and miscellaneous subclasses, such as methyl hydrazine derivatives and amidoximes. Useful biotherapeutics include monoclonal antibodies; monoclonal antibody cytotoxic conjugates of drugs and toxins, for example, ricin A chain or pokeweed antiviral protein; cytokines; biologic response modifiers; lymphokines; interferons; interleukins; growth factors; growth factor inhibitors; natural, recombinant, and synthetic proteins, enzymes, peptides, and nucleic acids and their functional equivalents. Useful radiotherapeutics include radioisotope labeled monoclonal antibodies, other radioisotope labeled tumor homing agents and metabolites exhibiting specific preference for tumors, and radioisotope labeled agents not displaying any tumor localization preference but having the solubility characteristics of the present invention.

Operationally, where cytotoxic, the antineoplastic agent is preferably dissolved in the organic solvent to a concentration such that when a therapeutically effective volume of the antineoplastic solution of the invention is delivered into a neoplastic mass, there results a dose of the agent solute in said mass of at least two logs greater than its tumoricidal dose 50% (TD50), that is, the concentration of agent in said mass that kills 50% of the tumor cells. This ensures that a supralethal concentration of the agent is delivered throughout at least a substantial volume of the tumor mass when the resulting antineoplastic solution is injected directly into the substance of the tumor. As the organic vehicle permeates the tumor mass it transports a therapeutically effective, neoplastically lethal concentration of the cytotoxic agent solute therewith. In this way high levels of the cytotoxic antineoplastic agent can be delivered discretely and with relative safety to the tumor mass. In another sense the water miscible organic vehicle component of the solution can be considered to increase the solubility of the agent within the tumor mass, thereby allowing therapeutically effective toxic levels of the antineoplastic agent to invest the tumor. It must also be appreciated that antineoplastic agents with high solubility in the water miscible organic solvent vehicles of the invention will themselves usually tend to have good cellular diffusivity characteristics and can thus, upon intratumoral administration, diffuse relatively efficiently on their own, perhaps even beyond the diffusion zone of the solvent vehicle component. The stability and bioavailability of the antineoplastic agent in the selected solvent vehicle aid in insuring that high levels of active drug permeate the tumor.

Many of the specific antineoplastic agents in current use have been, in part, chosen because of their high water solubility, thereby allowing them to be administered according to standard prior art delivery techniques. In accordance with the present invention, however, highly effective antineoplastic agents can be designed whose molecular architecture has been optimized for solubility, stability and/or bioavailability in one or more of the water miscible organic solvent vehicles of the invention. The present invention, therefore, defines a novel approach of rational drug design, formulation, and delivery.

In many instances, suitable antineoplastic agents already exist or are easily synthesized. For example, well known chemotherapeutic agents useful in the present invention include aceglatone, BCNU, busulfan, CCNU, chlorambucil, cactinomycin, carzinophilin, chlornaphazine, 6-chloropurine, cis-platinum, dactinomycin, demecolcine, ethylenimine quinone, hadacidin, lomustine, mechlorethamine, melphalan, Me-CCNU, plicamycin, mitotane, mycophenolic acid, nitracrine, nogalamycin, streptonigrin, streptozocin, tegafur, tetramin, testolactone, triaziquinone, 2,2,'2"-trichlorotriethylamine, trichodermin, triethylenephosphoramide, triethylenethiophosphoramide, ubenimex, urethan, vinblastine and vincristine. Antineoplastic peptides, proteins, enzymes and the like, which may not inherently possess proper solubility characteristics in their natural form, can be made more soluble in the organic solvent vehicles of the invention by incorporating suitable amino acid residues or sequences in their molecular architectures or by direct chemical modification. Even in the case of antisense nucleic acids, analogs with suitable organic solvent solubility characteristics can be synthesized as evidenced, for example, by the preparative work reported in "Inhibition of acquired immunodeficiency syndrome virus by oligdeoxynucleoside methyl phosphonates", Sarin et al., *Proceedings of the National Academy of Science USA* 85 (1988), pp. 7448-7451. Useful radioisotopes include phosphorus-32, yttrium-90, cobalt-60, gold-198, iridium-192, iodine-130, iodine-131, iodine-132, tantalum-182, copper-67, sulfur-35, and sodium-24.

Under some circumstances the water miscible organic solvent vehicles of the invention may exert direct cytotoxic effects themselves or exert a cooperative toxic effect on tumor masses treated therewith when combined with appropriate antineoplastic agents. Of course, mixtures of mutually compatible water miscible organic solvent vehicles as well as mixtures of compatible antineoplastic agent solutes may also be utilized and are specifically contemplated herein.

Antineoplastic agents previously considered too toxic for use with conventional prior art delivery methods may now be found useful under the present invention. This is so because the side toxicities of the resulting antineoplastic solutions are not as severe as can be encountered when delivered by standard extratumoral delivery methods since so little agent will reach systemic sites of toxicity. Antineoplastic agents may also be tailored to exhibit high stability in the water miscible organic solvent vehicles but be rather unstable in aqueous solution (for instance, BCNU is stable in ethanol but has a half life in serum of only about 15 minutes). In addition to being greatly diluted out, such antineoplastic agents will also be at least partially inactivated before reaching systemic sites of toxicity should the agents permeate the tumor and diffuse into surrounding healthy tissue. Of course, for a given tumor type an antineoplastic agent should be chosen which has a high toxicity for that tumor. In this way, as in the example below, the tumor can be dosed with cytotoxic levels several orders of magnitude greater than the tumoricidal dose 50%.

The illustrative non-limiting example below clearly demonstrates that, if properly localized, antineoplastic solutions formulated and used in accordance with the present invention can cure tumors. The solutions can be injected directly into neoplastic targets with great precision using computed tomograpy, ultrasound, gamma camera imaging, positron emission tomography or magnetic resonance tumor imaging. In addition to standard needles for delivery, the newer flexible skinny needles can also be found useful instruments.

While the present study of the working example utilized a single intratumoral injection, plural injections into separate tumor regions may prove more effective in investing the entire tumor mass with a therapeutically effective dose of the agent. Likewise, the total dose, concentration, volume of formulation delivered, and rate of delivery can be optimized for a given tumor type, size and architecture. The zone of toxicity can be controlled precisely by optimizing these parameters. The volume and concentration of the antineoplastic solutions delivered into the tumor mass must be sufficient to bring lethal levels of the agent solute throughout the tumor. Depending upon the vehicle, solubility of the antineoplastic agent, the number of injections, and their placement with respect to tumor architecture, it can be useful to administer total formulation volumes less than the tumor volume, greater than the tumor volume, or approximately equal to the tumor volume. In those cases where the vehicle solvent volume is not sufficient to perfuse the entire tumor, optimal solubility characteristics of the preferred antineoplastic agents, as described above, will encourage further facile diffusion of the agent throughout the tumor mass.

It is well known that surgical intervention in neoplastic treatment can seed tumor cells locally and into the blood stream and this may indeed be a genesis of recurrences and metastases in gliomas and other neoplasms. In accordance with the present invention this problem is ameliorated or eliminated since tumor cells shed by the injection incision(s) are likely to be within the treatment volume as the antineoplastic solution radiates from the needle orifice.

Although the method described preferably uses a needle to deliver the solution, an implantable device may also be utilized. However, any such device must permit the vehicle and antineoplastic agent to exit at similar rates so as to permit the organic solvent vehicle to convey therapeutically effective doses of the agent throughout the tumor. Needle delivery also has the advantage of accessing a large treatment volume while requiring only a small incision. This can be particularly important for inoperable tumors Neoplasms arising in all parts of the body can be treated using the present invention. These include primary and metastatic tumors of the brain, colon, rectum, breast, lung, ovaries, pancreas, stomach, uterus, testicles, nerve tissues and the like.

The advantages of the present invention can be seen by reference to the following illustrative example in which an antineoplastic solution is formulated according to the invention using ethanol as the organic solvent vehicle and BCNU as the antineoplastic agent solute. Ethanol is water miscible and diffuses effectively through cellular membranes. BCNU is soluble to highly cytotoxic levels in ethanol and remains stable and bioavailable therein. This exemplary therapeutic agent composition solution allows the tumor model to be treated with BCNU concentrations several logs greater than those realized using conventional methods of delivery. The efficacy of this solution and the direct intratumoral method of delivery thereof is evidenced by the results obtained. A single stereotactically fixed intratumoral injection of this solution produces a 41% cure rate, i.e., 23 of 56 animals treated, with a 433% increase in life span (ILS). This result is all the more suprising in view of the fact that the injection strategy employed for control purposes did not at all take into account the size or architecture of the tumor masses treated. Until the experiment of the working example was conducted, neither BCNU nor any other single antineoplastic agent has ever been known to produce a single cure in this tumor model irrespective of the mode of delivery to the tumor site.

EXAMPLE

Tumor

The T9 gliosarcoma was used in this study. The T9 was maintained in monolayer tissue culture in Falcon plastic flasks. Flasks contained Eagle's minimal essential medium (Gibco) supplemented with 20% newborn calf serum, non-essential amino acids, L-glutamine, and an antibiotic-antimycotic solution containing penicillin, streptomycin, and amphotericin B. The cultures were incubated at 37° C. in a high humidity atmosphere containing 5% carbon dioxide. When cells formed a monolayer and became confluent, they were trypsinized (0.25% trypsin, 0.2% ethylenediaminetetra-acetic acid) and subcultured. Aliquots of cells from various passages were kept frozen in liquid nitrogen with 10% (volume) glycerin.

Animals

Male CDF rats (Fischer 344) weighing 159-200 gm (Taconic Farms, Germantown, N.Y.) aged 60-80 days, were allowed to acclimate to laboratory conditions for one to two weeks prior to studies. They were given Purina rat chow and water, ad libitum, and maintained six per cage in a room with a light-dark cycle (12 hours on, 12 hours off). All experimental procedures were performed between 9AM and 7PM.

Intracerebral Tumor Implantation

T9 cells were trypsinized, harvested from their flasks and suspended in phosphate buffered saline. Cells were counted in a hemocytometer and viability was determined by the trypan blue exclusion method. Immediately prior to implantation, cells were drawn up into a Hamilton microliter syringe (#702) equipped with a 25 gauge needle. Seven hundred thousand tumor cells in a volume of 10 ul were injected stereotactically into the right caudate hemisphere of each animal. For this tumor inoculation, animals were anesthetized on day zero (0) with pentobarbital sodium (25-30 mg/kg) intraperitoneally and placed into a stereotactic frame. The head was shaved, a midline longitudinal scalp incision was made, and the bregma identified. Using a dental drill, a 1 mm burr hole was placed 3 mm to the right of the bregma and 1 mm posterior to the coronal suture. Next the needle tip was lowered into the cerebrum to a depth of 5 mm below the dural surface and then retracted 1 mm. The purpose of this retraction procedure was to create a small pocket into which the cells could be injected. The needle bevel was positioned to face laterally in order to mitigate against inadvertant intraventricular injection. Cells were injected slowly over a period of 2 minutes. The needle was then withdrawn and the burr hole sealed with bone wax. The operative field was cleaned with povidone-iodine solution and the scalp incision was closed with clips.

Antineoplastic Solution

A solution of BCNU (Carmustine) Bristol Laboratories, Syracuse, N.Y.) was prepared by dissolving 100 mg thereof in 1.5 ml absolute ethanol. All intratumoral injections used this 66.7 mg/ml formulation directly. This concentration is about three to four logs greater than the tumoricidal dose 50%. The dose delivered to each animal was 5 mg BCNU/kg body weight. Accordingly, a rat weighing 180 gm received 13.5 ul, equivalent to a total dose of 0.9 mg BCNU. For animals additionally receiving 5 mg BCNU/kg body weight intraperitoneally, this 66.7 mg/ml solution was further diluted to 5 mg/ml with sterile water immediately preceding its use. This is a relatively low dose, and approximates 40% of the LD10 determined for intraperitoneal BCNU in rats. A dose of 5 mg BCNU/kg is equivalent to 30 mg/square meter) for a rat. This cannot be extrapolated to man, however, because of differences in cross-species toxicity.

Intratumoral BCNU

Rats were anesthetized with ether and pentobarbital sodium (25-30 mg/kg) and placed into the stereotactic frame. The clips and bone wax were carefully removed. The BCNU solution was delivered directly into the tumor through a
Hamilton microsyringe set to the same coordinates and using the same technique as used in the initial tumor implantation. As before, the operative field was cleaned with povidone-iodine solution and the scalp was closed with clips.

Treatment

The following paradigm was used to assess therapeutic efficacy of the intra-tumorally delivered BCNU antineoplastic solution. All animals received tumor implantation on day zero (0). Controls received no treatment, vehicle controls received a single intratumoral injection of absolute ethanol on day 7. One experimental group received a single injection of intratumoral BCN dissolved in absolute ethanol at a dose of 5 mg/kg body weight on day 7. A second experimental group received a single intratumoral BCNU injection of 5 mg/kg body weight on day 7, followed by a second dose of BCNU (5 mg/kg body weight) delivered intraperitoneally on day 12.

Evaluation

Using length of survival as an endpoint, the efficacy of the two therapeutic regimens was compared. All animals were autopsied at their time of death. A gross inspection was made of the lungs, liver and kidneys, and the brain was removed in toto and fixed in 10% buffered formalin for three days. A single coronal section was cut through the center of the tumor site and both halves were imbedded in paraffin and stained with hematoxylin and eosin for blind histopathologic examination. Median survival rates were calculated for each group, and the data were analyzed nonparametrically with the Wilcoxon rank sum test. The twenty-three animals classified as cured include nineteen animals living a normal lifespan, i.e., 600-700 days and four animals sacrificed healthy for histology on days 121, 136, 307, 384, and demonstrating no observable viable T9 gliosarcoma.

Results

Operative mortality was 4.7% (4/86) for tumor bearing animals following sodium pentobarbital administration but preceding intratumoral injection, 7.1% (1/14) following intratumoral vehicle injection, and 5.5.% (4/72) following intratumoral BCNU solution injection.

Survival data are summarized in Table 1, below. Control animals (n=35) live a median of 18 days. Vehicle controls (n=13) live a median of 17 days. One of the vehicle control animals lived a normal life span and was considered cured (8%).

Animals that received a single intratumoral injection of the BCNU antineoplastic solution (n=42) live a median of 76 days, i.e., an increased life span of 322%, $p<10-6$.

TABLE 1

| Survival Data for Rats bearing T9 Gliosarcoma. | | | | | | | |
|---|---|---|---|---|---|---|---|
| Grp | Rx | n | MDS | % ILS | Cures | % Cures | p |
| 1 | None | 35 | 18 | — | 0 | 0 | — |
| 2 | ETOH | 13 | 17 | 0 | 1 | 8 | NS |
| 3 | BCNU/ ETOH IT | 42 | 76 | 322 | 18 | 43 | <10−6 ⎤<br>⎥ NS<br>⎥ |
| 4 | BCNU/ ETOH IT + BCNU/ ETOH + H2O IP | 14 | 103 | 472 | 5 | 36 | <10−6 ⎦ |

TABLE 1-continued

Survival Data for Rats bearing T9 Gliosarcoma.

| | | | | | | | |
|---|---|---|---|---|---|---|---|
| 3 + | AS | 56 | 96 | 433 | 23 | 41 | <10−6 |
| 4 | ABOVE | | | | | | |

Grp - group; Rx - treatment received, Group 1 were controls that received no treatment following tumor implantation, Group 2 were vehicle controls that received a single intratumoral injection of absolute ethanol on day 7, Group 3 received a single intratumoral injection (IT) of BCNU dissolved in absolute ethanol at a dose of 5 mg/kg on day 7, Group 4 received a single intratumoral injection (IT) of BCNU (5 mg/kg) in absolute ethanol on day 7, followed by an intraperitoneal injection (IP) of BCNU (5 mg/kg) in 7.5% aqueous ethanol on day 12; n - number of animals in each group MDS - median day of survival following tumor implantation; % ILS - percent increase in life span = (median day of survival for treated group - median day of survival for control group/median day of survival for control group) × 100; Cures - the group 2 animal was sacrificed healthy on day 614 for histology; the twenty-three animals in groups 3 + 4 include nineteen animals living normal lifespan, i.e., 600-700 days, and four animals sacrificed healthy on days 121, 136, 307, 384 and not demonstrating T9 gliosarcoma; p - statistical significance as determined by the Wilcoxen rank sum test; NS - not significant.

Eighteen of the forty-two animals were cured (43%).

Animals that received a single intratumoral injection of the BCNU antineoplastic solution followed by intraperitoneal BCNU (n=14) live a median of 103 days, i.e., an increased life span of 472%, $p<10-6$. Five animals were cured (36%). The addition of the intraperitoneal BCNU to the treatment regimen did not statistically enhance the therapeutic benefit of the primary intratumoral BCNU solution injection.

Considered as one group, the fifty-six animals that received a single intratumoral injection of BCNU solution live a median survival of 96 days, i.e., an increase in life span of 433%, $p<10-6$. Twenty-three animals were cured (41%).

Figure 1:
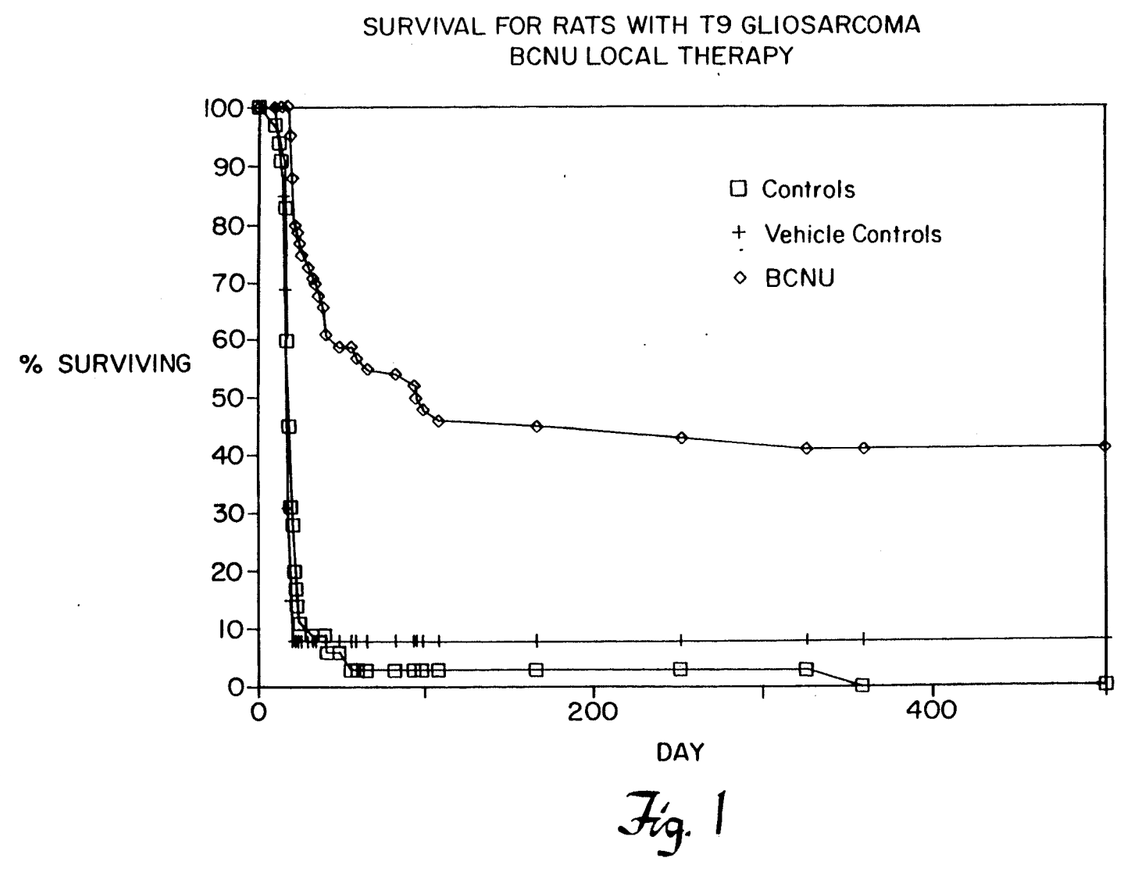
FIG. 1 is a graph illustrating the results obtained in the working example hereof wherein treatment of an experimental brain tumor was effected using a specific antineoplastic solution formulated and used according to the invention.

Survival curves are shown in FIG. 1. Both control and vehicle treated groups demonstrate essentially one steep phase with 90% of the animals dying between days 9 to 24. In contrast, the intratumoral BCNU solution treated group demonstrates four phases, i.e, an initial steep phase in which 23% of the animals die between days 18-24; a second less steep phase in which 30% of the animals die between days 25 to 166; a third shallow phase in which 5% of the animals die between days 251-325 and a fourth phase or group comprising 41% which live a normal life span, i.e., 600-700 days.

The growth of the untreated and treated T9 gliosarcoma is described as follows. Day seven was chosen for treatment. The average size of the tumor and the fact that animals began dying as early as day nine indicates the severe therapeutic challenge posed by the present model. If untreated, tumors grew into very large masses typically replacing an entire hemisphere in cross section, and often larger. The tumors sometimes appeared as a single lobe but often grew in multi-lobular fashion demonstrating both upper and lower lobes. The tumors were very healthy and densely cellular with many mitoses.

Vehicle controls also demonstrated tumors the size of a hemisphere at death. However, cysts were usually found, often accompanied by necrosis, polymorphonuclear leukocytes and some hemorrhage, presumably marking the site of injection.

BCNU treated animals which died during phase one, i.e., 18-24 days, displayed typical large healthy tumors. However, tumor cell necrosis was also observed, usually at top of the tumor while the bottom grew out aggressively. Cysts with polymorphonuclear leukocytes and sometimes hemorrhage were found.

Most BCNU treated animals that died during phase 2, i.e., 25-166 days displayed large tumors containing prominent bands of central necrosis. Three which lived relatively long, i.e., 94, 108 and 98 days, did not. Two of these histologically presented acute hemorrhage and no tumor, while the third displayed a large cyst with polymorphonuclear leukocytes and some very unhealthy T9 tumor tissue. This latter animal also had a lung infection.

The BCNU treated animals that died during phase 3, i.e., days 251-325, demonstrated cysts, necrosis, scar tissue, and no T9 gliosarcoma, cause(s) of death unknown.

BCNU treated animals which lived a normal life span, i.e., 600-700 days, displayed large cysts always surrounded by dense connective tissue capsules, some containing polymorphonuclear leukocytes. Although no T9 gliosarcoma tumor was found, tumor cell necrosis was usually present as was hemosiderin pigment. Some animals also presented with extensive infiltrates of lymphocytes and plasma cells. The one vehicle control animal which lived a normal life span displayed this same histology.

To study acute effects on the tumor some of the intratumoral solution BCNU treated animals (n=12) were sacrificed healthy on days 7, 10 and 14. Histology demonstrated that these animals could be placed into one of three groups. One group displayed tumor destruction at the top, with the majority of the tumor left untouched. In a second group most of the tumor was successfully treated, but small amounts of viable tumor remained. In a third group the tumor was totally eradicated by the therapy and was replaced with a cyst containing necrotic tumor tissue.

These data demonstrate that a single intratumoral injection of BCNU dissolved in a vehicle of absolute ethanol produces a 41% cure rate of T9 gliosarcoma. These results are striking in that neither BCNU nor any other antineoplastic agent has ever produced cures in animals bearing this tumor. It has been previously reported, "Effect of difluoromethylornithine on the antiglioma therapeutic efficacy of intra-arterial BCNU", Cohen et. al. *Journal of Neurosurgery* 65 (1986) pp. 671-678, that the same BCNU dose, i.e., 5 mg/kg body weight, produced no improvement in life span when delivered systemically, and produced an ILS of 57% when delivered intra-arterially. Other workers reported that at a higher dose, i.e., 13.3 mg/kg (lethal dose 10%), BCNU produced a modest ILS of 180% delivered either intravenously or intra-arterially. The relative ineffectiveness of BCNU introduced into the circulatory system in this and other primary brain tumor models parallels its poor efficacy in humans The results of the current study demonstrate that intratumoral delivery of highly concentrated BCNU in a water soluble organic solvent vehicle represents a far more effective treatment.

The effectiveness of the method is at least partially based upon the supralethal concentrations of active BCNU delivered directly to the tumor while at the same time only minimal levels of active drug reach systemic sites of toxicity.

Histology demonstrated that the direct intratumoral BCNU solution treatment totally eradicated the tumors in animals which lived a normal life span. On the other hand, the single 4 mm deep injection protocol employed did miss a portion of the tumor in most animals which did not live a normal life span. This variability is not suprising considering that: a) drug injection was "aimed" by using the same stereotactic coordinates utilized for tumor implantation, and b) tumor often did not grow exclusively at this site but rather as multiple lobes. Often, the upper lobe was found eliminated but a bottom lobe was missed.

These data as well as some other observations suggest that when delivered deep into the tumor the formulation exhibited preferential diffusion within the tumor. In this regard, a) minimal necrosis of normal tissue was observed, and b) the size and geometry of the lesions induced by the drug injection were reminiscent of the size and geometry of tumors seen on day seven by histology. The common vasculature of tumor masses as somewhat distinct from the surrounding normal brain may, in part, be responsible for these findings.

The example described above is merely illustrative of the present invention. That many other useful antineoplastic solutions can be formulated and delivered intratumorally according to the present invention will be apparent to those skilled in the art. Therefore, the present invention is to be considered as limited only by the appended claims.

I claim:

1. A method for treating neoplastic masses with comprises at least once injecting directly into a neoplastic mass a therapeutically effective volume of an antineoplastic solution consisting essentially of an organic, water miscible solvent vehicle and a therapeutically effective concentration of an antineoplastic agent solute, said organic, water miscible solvent vehicle having a partition coefficient of at least about 0.1 and said antineoplastic agent being effectively stable and bioavailable in said solvent vehicle.

2. The method of claim 1 wherein said antineoplastic agent solute is a cytotoxic agent.

3. The method of claim 2 wherein the dose of cytotoxic antineoplastic agent solute injected into the neoplastic mass is at least two logs greater than the TD50.

4. The method of claim 2 wherein said antineoplastic agent solute is a nitrosourea.

5. The method of claim 2 wherein said antineoplastic agent solute is BCNU.

6. The method of claim 1 wherein said solvent vehicle has a molecular weight no greater than about 1000 Daltons and electrical neutrality.

7. The method of claim 1 wherein said solvent vehicle is an aliphatic alcohol having a maximum of four carbon atoms.

8. The method of claim 7 wherein said aliphatic alcohol is ethanol.

9. The method of claim 8 wherein said ethanol is absolute alcohol.

10. The method of claim 1 wherein treatment of the neoplastic mass in undertaken as a plurality of injections of said antineoplastic solution into different regions of said mass.

11. An antineoplastic solution for the treatment of neoplastic masses by direct intratumoral delivery thereof, said solution consisting essentially of an organic, water miscible solvent vehicle having a partition coefficient of at least about 0.1 and a therapeutically effective concentration of an antineoplastic agent solute, said solute being effectively stable and bioavailable in said solvent vehicle.

12. The antineoplastic solution of claim 11 wherein said solvent vehicle has a molecular weight no greater than about 1000 Daltons and electrical neutrality.

13. The antineoplastic solution of claim 12 wherein said solvent vehicle is an aliphatic alcohol having a maximum of four carbon atoms.

14. The antineoplastic solution of claim 13 wherein said aliphatic alcohol is ethanol.

15. The antineoplastic solution of claim 11 wherein said antineoplastic agent solute is a nitrosourea.

16. The antineoplastic solution of claim 15 wherein said antineoplastic agent solute is BCNU.

17. An antineoplastic solution for the treatment of neoplastic masses by direct intratumoral delivery thereof, said solution consisting essentially of an organic, water miscible solvent vehicle having a partition coefficient of at least about 0.1 and a therapeutically effective concentration of a cytostatic antineoplastic agent solute, said solute being effectively stable and bioavailable in said solvent vehicle.

18. The antineoplastic solution of claim 17 wherein said solvent vehicle has a molecular weight no greater than about 1000 Daltons and electrical neutrality.

19. The antineoplastic solution of claim 18 wherein said solvent vehicle is an aliphatic alcohol having a maximum of four carbon atoms.

20. The antineoplastic solution of claim wherein said aliphatic alcohol is ethanol.

21. An antineoplastic solution for the treatment of neoplastic masses by direct intratumoral delivery thereof, said solution consisting essentially of an organic, water miscible solvent vehicle having a partition coefficient of at least about 0.1 and a therapeutically effective concentration of an alkylating agent solute selected from the group consisting of platinum coordination compounds, nitrogen mustards, ethyleneimine derivatives, alkyl sulfonates, triazenes or combinations thereof, said solute being effectively stable and bioavailable in said solvent vehicle.

22. The antineoplastic solution of claim 21 wherein said solvent vehicle has a molecular weight no greater than about 1000 Daltons and electrical neutrality.

23. The antineoplastic solution of claim 22 wherein said solvent vehicle is an aliphatic alcohol having a maximum of four carbon atoms.

24. The antineoplastic solution of claim 23 wherein said aliphatic alcohol is ethanol.

25. The antineoplastic solution of claim 21 wherein said alkylating agent solute is cytotoxic and is present in said solution at a concentration such that the resulting does thereof in a neoplastic mass when delivered thereinto as one or more injections thereof is at least two logs greater than the TD50.

26. An antineoplastic solution for the treatment of neoplastic masses by direct intratumoral delivery thereof, said solution consisting essentially of an organic, water miscible solvent vehicle having a partition coefficient of at least 0.1 and a therapeutically effective concentration of a biotherapeutic or radiotherapeutic agent solute, said solute being effectively stable and bioavailable in said solvent vehicle.

27. The antineoplastic solution of claim 26 wherein said solvent vehicle has a molecular weight no greater than about 1000 Daltons and electrical neutrality.

28. The antineoplastic solution of claim 27 wherein said solvent vehicle is an aliphatic alcohol having a maximum of four carbon atoms.

29. The antineoplastic solution of claim 28 wherein said aliphatic alcohol is ethanol.

30. The antineoplastic solution of claim 26 wherein said biotherapeutic or radiotherapeutic agent solute is cytotoxic and wherein said solute is present in said solution at a concentration such that the resulting dose thereof in a neoplastic mass when delivered thereinto as one or more injections thereof is at least two logs greater than the TD50.

31. An antineoplastic solution for the treatment of neoplastic masses by direct intratumoral delivery thereof, said solution consisting essentially of an organic, water miscible solvent vehicle having a partition coefficient of at least about 0.1 and a therapeutically effective concentration of a chemotherapeutic agent solute selected from the group consisting of antimetabolites, vinca alkaloids, antibiotics, hormones or combinations thereof, said solute being effectively stable and bioavailable in said solvent vehicle.

32. The antineoplastic solution of claim 31 wherein said solvent vehicle has a molecular weight no greater than about 1000 Daltons and electrical neutrality.

33. The antineoplastic solution of claim 32 wherein said solvent vehicle is an aliphatic alcohol having a maximum of four carbon atoms.

34. The antineoplastic solution of claim 33 wherein said aliphatic alcohol is ethanol.

35. The antineoplastic solution of claim wherein said chemotherapeutic agent solute is cytotoxic and wherein said solute is present in said solution at a concentration such that the resulting dose thereof in a neoplastic mass when delivered thereinto as one or more injections thereof is at least two logs greater than the TD50.

* * * * *

UNITED STATES PATENT AND TRADEMARK OFFICE
CERTIFICATE OF CORRECTION

PATENT NO. : 5,162,115

DATED : November 10, 1992

INVENTOR(S) : Dennis D. Pietronigro

It is certified that error appears in the above—identified patent and that said Letters Patent is hereby corrected as shown below:

Column 13, line 44, "with" should read -- which --. Column 14, line 44, after "claim" insert -- 19 --; line 68, "does" should read -- dose --. Column 16, line 19, after "claim" insert -- 31 --.

Signed and Sealed this

Fifth Day of October, 1993

Attest:

BRUCE LEHMAN

Attesting Officer

Commissioner of Patents and Trademarks